United States Patent [19]

Lindig et al.

[11] Patent Number: 4,948,417
[45] Date of Patent: Aug. 14, 1990

[54] HERBICIDAL SUBSTITUTED TRIAZOLINONES

[75] Inventors: Markus Lindig, Hilden; Karlfried Dickore, Leverkusen; Kurt Findeisen, Odenthal; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 212,835

[22] Filed: Jun. 29, 1988

[30] Foreign Application Priority Data

Jul. 10, 1987 [DE] Fed. Rep. of Germany ....... 3722821

[51] Int. Cl.$^5$ ................. C07D 249/12; A01N 43/653
[52] U.S. Cl. ........................................ 71/92; 548/263.2
[58] Field of Search .................... 548/263, 265; 71/74, 71/92

[56] References Cited

FOREIGN PATENT DOCUMENTS 0140194  5/1985  European Pat. Off. .
0146279  6/1985  European Pat. Off. .
2707801  9/1977  Fed. Rep. of Germany .
7833549  5/1978  South Africa ...................... 548/265

OTHER PUBLICATIONS

George et al., "Heterocycles from N–Ethoxy etc.", CA 85:143036g, (1976).

Primary Examiner—Glennon H. Hollrah
Assistant Examiner—Patricia L. Morris
Attorney, Agent, or Firm—Sprung Horn Kramer & Woods

[57] ABSTRACT

Herbicidal substituted triazolinones of the formula

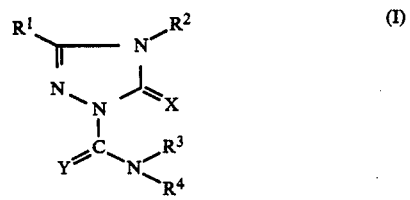

in which
$R^1$ represents hydrogen, alkyl, alkenyl, alkynyl, halogenoalkyl, halogenoalkenyl, halogenoalkynyl, alkoxyalkyl, alkoxy, cycloalkylalkyl, cycloalkyl or in each case optionally substituted aralkyl or aryl,
$R^2$ represents alkyl, alkenyl, alkynyl, halogenoalkyl, halogenoalkenyl, halogenoalkynyl, alkoxyalkyl, alkoxy, cycloalkylalkyl, cycloalkyl or in each case optionally substituted aralkyl or aryl,
$R^3$ and $R^4$ independently of one another each represent hydrogen, alkyl, alkenyl, alkynyl, halogenoalkyl, halogenoalkenyl, halogenoalkinyl, cyanoalkyl, hydroxyalkyl, alkoxyalkyl, alkoximinoalkyl, alkoxycarbonylalkyl, alkoxycarbonylalkenyl, alkylaminoalkyl, dialkylaminoalkyl, in each case optionally substituted cycloalkyl, cycloalkylalkyl, cyclcalkenyl or cycloalkenylalkyl, optionally substituted heterocyclylalkyl, in each case optionally substituted aralkyl, aroyl or aryl, alkoxy, alkenyloxy, alkynyloxy, aralkyloxy or aryloxy or, together with the nitrogen atom to which they are bonded, represent an optionally substituted heterocycle,
X represents oxygen or sulphur and
Y represents oxygen or sulphur,
where X represents sulphur only, when at least one of the radicals $R^3$ or $R^4$ does not simultaneously represent hydrogen, methyl or ethyl.

5 Claims, No Drawings

HERBICIDAL SUBSTITUTED TRIAZOLINONES

The invention relates to new substituted triazolimones, several processes for their preparation and their use as herbicides.

It has been disclosed that certain nitrogen heterocycles such as, for example, N-isobutyl-imidazolidin-2-one-1-carboxamide possess herbicidal properties (compare, for example, K. H. Bochel "Pflanzenschutz und Schädlingsbekämpfung" ("Plant Protection and Pest Combating") p.170, Thieme Verlag Stuttgart 1977).

However, the herbicidal activity of these previously known compounds with respect to problem weeds as well as their toleration by important cultivated plants is not completely satisfactory in all areas of application.

Furthermore, certain substituted triazolinethiones have been disclosed (compare DE-OS (German Published Specification) No. 2,707,801).

Nothing has hitherto been disclosed about a herbicidal activity of the previously known triazolinethiones.

New substituted triazolinones of the general formula (I)

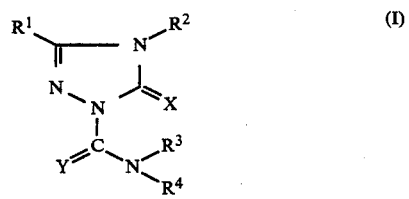

in which
R$^1$ represents hydrogen, alkyl, alkenyl, alkinyl, halogenoalkyl, halogenoalkenyl, halogenoalkinyl, alkoxyalkyl, alkoxy, cycloalkylalkyl, cycloalkyl or in each case optionally substituted aralkyl or aryl,
R$^2$ represents alkyl, alkenyl, alkinyl, halogenoalkyl, halogenoalkenyl, halogenoalkinyl, alkoxyalkyl, alkoxy, cycloalkylalkyl, cycloalkyl or in each case optionally substituted aralkyl or aryl,
R$^3$ and R$^4$ independently of one another each represent hydrogen, alkyl, alkenyl, alkinyl, halogenoalkyl, halogenoalkenyl, halogenoalkinyl, cyanoalkyl, hydroxyalkyl, alkoxyalkyl, alkoximinoalkyl, alkoxycarbonylalkyl, alkoxycarbonylalkenyl, alkylaminoalkyl, dialkylaminoalkyl, in each case optionally substituted cycloalkyl, cycloalkylalkyl, cycloalkenyl or cycloalkenylalkyl, optionally substituted heterocyclylalkyl, in each case optionally substituted aralkyl, aroyl or aryl, alkoxy, alkenyloxy, alkinyloxy, aralkyloxy or aryloxy or, together with the nitrogen atom to which they are bonded, represent an optionally substituted heterocycle,
X represents oxygen or sulphur and
Y represents oxygen or sulphur,
where X only represents sulphur, however, when at least one of the radicals R$^3$ or R$^4$ does not simultaneously represent hydrogen, methyl or ethyl, have been found.

The compounds of the formula (I) can exist, where appropriate, as geometric and/or optical isomers or isomeric mixtures of variable composition, depending on the type of the substituents R$^1$, R$^2$, R$^3$ and R$^4$ Both the pure isomers and the isomeric mixtures are claimed according to the invention.

Furthermore, it has been found that the new substituted triazolinones of the general formula (I)

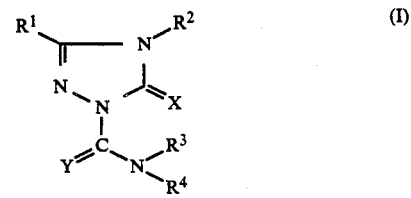

in which
R$^1$ represents hydrogen, alkyl, alkenyl, alkinyl, halogenoalkyl, halogenoalkenyl, halogenoalkinyl, alkoxyalkyl, alkoxy, cycloalkylalkyl, cycloalkyl or in each case optionally substituted aralkyl or aryl, R$^2$ represents alkyl, alkenyl, alkinyl, halogenoalkyl, halogenoalkenyl, halogenoalkinyl, alkoxyalkyl, alkoxy, cycloalkylalkyl, cycloalkyl or in each case optionally substituted aralkyl or aryl,
R$^3$ and R$^4$ independently of one another each represent hydrogen, alkyl, alkenyl, alkinyl, halogenoalkyl, halogenoalkenyl, halogenoalkinyl, cyanoalkyl, hydroxyalkyl, alkoxyalkyl, alkoximinoalkyl, alkoxycarbonylalkyl, alkoxycarbonylalkenyl, alkylaminoalkyl, dialkylaminoalkyl, in each case optionally substituted cycloalkyl, cycloalkylalkyl, cycloalkenyl or cycloalkenylalkyl, optionally substituted heterocyclylalkyl, in each case optionally substituted aralkyl, aroyl or aryl, alkoxy, alkenyloxy, akinyloxy, aralkyloxy or aryloxy or, together with the nitrogen atom to which they are bonded, represent an optionally substituted heterocycle,
X represents oxygen or sulphur and
Y represents oxygen or sulphur,
where X only represents sulphur, however, when at least one of the radicals R$^3$ or R$^4$ does not simultaneously represent hydrogen, methyl or ethyl, are obtained when
(a) 1-chloro-(thio)carbonyltriazolinones of the formula (II)

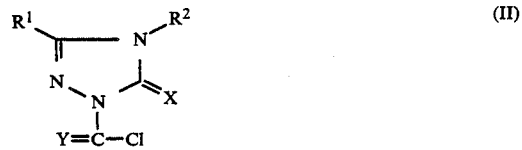

in which
R$^1$, R$^2$, X and Y have the above-mentioned meaning, are reacted with amines of the formula (III)

in which
R$^3$ and R$^4$ have the above-mentioned meaning, if desired in the presence of a diluent and if desired in the presence of an acid-binding agent, or
(b) in the case where R$^3$ denotes hydrogen, when 1-unsubstituted triazolinones of the formula (IV)

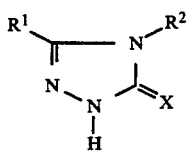

in which
R$^1$, R$^2$ and X have the above-mentioned meaning, are reacted with iso(thio)cyanates of the formula (V)

in which
R$^4$ and Y have the above-mentioned meaning, if desired in the presence of a diluent and if desired in the presence of a reaction auxiliary.

Finally, it has been found that the new substituted triazolinones of the general formula (I) possess herbicidal properties.

Surprisingly, the substituted triazolinones of the general formula (I) according to the invention show a considerably higher herbicidal potency against problem weeds than the nitrogen heterocycles known from the prior art such as, for example, N-isobutyl-imidazolin-2-one-1-carboxamide, which are related compounds chemically and with respect to their action.

Formula (I) provides a general definition of the substituted triazolinones according to the invention. Preferred compounds of the formula (I) are those in which
R$^1$ represents hydrogen or represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, or alkoxyalkyl or alkoxy each having 1 to 6 carbon atoms in the individual alkyl parts, or represents cycloalkylalkyl or cycloalkyl each having 3 to 7 carbon atoms in the cycloalkyl part and optionally 1 to 6 carbon atoms in the straight-chain or branched alkyl part, or aralkyl or aryl, each having 6 to 10 carbon atoms in the aryl part and optionally 1 to 6 carbon atoms in the straight-chain or branched alkyl part, which are each optionally monosubstituted or polysubstituted by identical or different substituents, suitable substituents on aryl being in each case: halogen, cyano, nitro, and in each case straight-chain or branched alkyl, alkoxy, alkylthio, halogenoalkyl, halogenoalkoxy or halogenoalkylthio, each having 1 to 4 carbon atoms and optionally 1 to 9 identical or different halogen atoms,
R$^2$ represents In each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, alkoxyalkyl or alkoxy, each having 1 to 6 carbon atoms in the individual alkyl parts, cycloalkylalkyl or cycloalkyl, each having 3 to 7 carbon atoms in the cycloalkyl part and optionally 1 to 6 carbon atoms in the straight-chain or branched alkyl part, or aralkyl or aryl, each having 6 to 10 carbon atoms in the aryl part and optionally 1 to 6 carbon atoms in the straight-chain or branched alkyl part, which are each optionally monosubstituted or polysubstituted by identical or different substituents, suitable substituents on aryl being in each case: halogen, cyano, nitro, and straight-chain or branched alkyl, alkoxy, alkylthio, halogenoalkyl, halogenoalkoxy or halogenoalkylthio, each having 1 to 4 carbon atoms and optionally 1 to 9 identical or different halogen atoms, R$^3$ and R$^4$ independently of one another each represent hydrogen or represent in each case straight-chain or branched alkyl having 1 to 18 carbon atoms, alkenyl having 2 to 8 carbon toms, alkinyl having 2 to 8 carbon atoms, halogenoalkyl having 1 to 8 carbon atoms and 1 to 17 identical or different halogen atoms, halogenoalkenyl or halogenoalkinyl, each having 2 to 8 carbon atoms and 1 to 15 or 13 identical or different halogen atoms respectively, cyanoalkyl having 1 to 8 carbon atoms, hydroxyalkyl having 1 to 8 carbon atoms and 1 to 6 hydroxyl groups, alkoxyalkyl, alkoximinoalkyl, alkoxycarbonylalkyl or alkoxycarbonylalkenyl, each having up to 6 carbon atoms in the individual alkyl or alkenyl parts, or alkylaminoalkyl or dialkylaminoalkyl, each having 1 to 6 carbon atoms in the individual alkyl parts, or represent cycloalkyl, cycloalkylalkyl, cycloalkenyl or cycloalkenylalkyl, each having 3 to 8 carbon atoms in the cycloalkyl or cycloalkenyl part and optionally 1 to 6 carbon atoms in the alkyl part, which are each optionally monosubstituted or polysubstituted by identical or different substituents, suitable substituents being in each case: halogen, cyano and straight-chain or branched alkyl or halogenoalkyl, each having optionally 1 to 4 carbon atoms and optionally 1 to 9 identical or different halogen atoms or bivalent alkanediyl or alkenediyl, each having up to 4 carbon atoms; and in addition heterocyclylalkyl having 1 to 6 carbon atoms in the straight-chain or branched alkyl part and 1 to 9 carbon atoms and also 1 to 3 heteroatoms—in particular nitrogen, oxygen and/or sulphur—in the heterocyclic part, which is optionally monosubstituted or polysubstituted in the heterocyclic part by identical or different substituents, suitable substituents being: halogen, cyano, nitro, and straight-chain or branched alkyl, alkoxy, alkylthio, halogenoalkyl, halogenoalkoxy, halogenoalkylthio or alkoxycarbonyl, each having 1 to 5 carbon atoms and optionally 1 to 9 identical or different halogen atoms; and in addition straight-chain or branched alkoxy having 1 to 8 carbon atoms, alkenyloxy having 2 to 8 carbon atoms or alkinyloxy having 2 to 8 carbon atoms, and finally aralkyl, aralkyloxy, aryloxy, aroyl or aryl, each having 6 to 10 carbon atoms in the aryl part and optionally 1 to 6 carbon atoms in the alkyl part, which are each optionally monosubstituted or polysubstituted by identical or different substituents, suitable substituents on aryl being in each case: halogen, cyano, nitro, hydroxyl, straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl, each having 1 to 6 carbon atoms and optionally 1 to 9 identical or different halogen atoms, cycloalkyl having 3 to 6 carbon atoms and phenoxy and where, if appropriate, suitable substituents on alkyl are: halogen or cyano, or $R^3$ and $R^4$, together with the nitrogen atom to which they are bonded, represent a five- to ten-membered heterocycle which can optionally contain 1 to 2 further heteroatoms, in particular nitrogen, oxygen and/or sulphur, and which is optionally monosubstituted or polysubstituted by identical or different substituents, suitable substituents being: halogen and in each case straight-chain or branched alkyl or halogenoalkyl, each having 1 to 4 carbon atoms and optionally 1 to 9 identical or different halogen atoms and 1 to 2 oxo- or thionogroups, X represents oxygen or sulphur and Y represents oxygen or sulphur, where X only represents sulphur, however, when at least one of the radicals $R^3$ or $R^4$ does not simultaneously represent hydrogen, methyl or ethyl.

Particularly preferred compounds of the formula (I) are those in which $R^1$ represents hydrogen, methyl, ethyl, n- or i-propyl, n-, i-, s- or t-butyl, n- or i-pentyl, n- or i-hexyl, allyl, propargyl, methoxy, ethoxy, methoxymethyl, ethoxymethyl, methoxyethyl, ethoxyethyl, straight-chain or branched halogenoalkyl having 1 to 4 carbon atoms and 1 to 9 identical or different halogen atoms, in particular fluorine, chlorine or bromine, cyclopentyl, cyclohexyl, cyclopropyl, cyclopropylmethyl, cyclohexylmethyl, cyclohexylethyl or benzyl or phenyl, which are each optionally monosubstituted to trisubstituted by identical or different substituents, suitable substituents being in each case: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, $R^2$ represents methyl, ethyl, n- or i-propyl, n-, i-, s- or t-butyl, n- or i-pentyl, n- or i-hexyl, allyl, propargyl, methoxy, ethoxy, methoxymethyl, ethoxymethyl, methoxyethyl, ethoxyethyl, straight-chain or branched halogenoalkyl having 1 to 4 carbon atoms and 1 to 9 identical or different halogen atoms, in particular fluorine, chlorine or bromine, cyclopentyl, cyclohexyl, cyclopropyl, cyclopropylmethyl, cyclohexylmethyl, cyclohexylethyl, or benzyl or phenyl, which are each optionally monosubstituted to trisubstituted by identical or different substituents, suitable substituents being in each case: fluorine, chlorine, bromine, cyano, nitro, methyl, ethyl, - or i-propyl, n-, i-, s- or t-butyl, methoxy, ethoxy, methylthio, trifluoromethyl, trifluoro methoxy or trifluoromethylthio, $R^3$ and $R^4$ independently of one another each represent hydrogen, methyl, ethyl, n- or i-propyl, n-, i-, s-or t-butyl, n-, or i-pentyl, n -or i-hexyl, n- or i-heptyl, n- or i-octyl, n- or i-nonyl, n- or i-decyl, n- or i-dodecyl, allyl, pro-penyl, n-or i-butenyl, n- or i-pentenyl, n- or i-hexenyl, propargyl, n-or i-butinyl, n- or i-pentinyl, n- or i-hexinyl, straight-chain or branched halogenoalkyl having 1 to 4 carbon atoms and 1 to 9 identical or different halogen atoms, in particular fluorine, chlorine or bromine, straight-chain or branched halogenoalkenyl or halogenoalkinyl, each having 3 to 5 carbon atoms and 1 to 3 halogenatoms in particular fluorine or chlorine; in each case straight-chain or branched cyanoalkyl having 1 to 4 carbon atoms in t having 1 to 6 carbon atoms and 1 to 3 hydroxyl groups, alkoxyalkyl, alkoximinoalkyl, alkoxycarbonylalkyl or alkoxycarbonylalkenyl, alkylaminoalkyl or dialkylaminoalkyl, each having up to 4 carbon atoms in the individual alkyl or alkenyl parts; or cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl or cyclohexenylmethyl, which are each optionally monosubstituted to trisubstituted by identical or different substituents, suitable substituents in the cyclic and where appropriate in the aliphatic part being in each case: fluorine, chlorine, bromine, methyl, ethyl, n-or i-propyl, n-, i-, s- or t-butyl, cyano, methanediyl, ethanediyl, butanediyl or butadienediyl; and additionally heterocyclylmethyl, heterocyclylethyl or heteocyclylpropyl, which are optionally monosubstituted to trisubstituted in the heterocyclic part by identical or different substituents, suitable heterocycles being in each case:

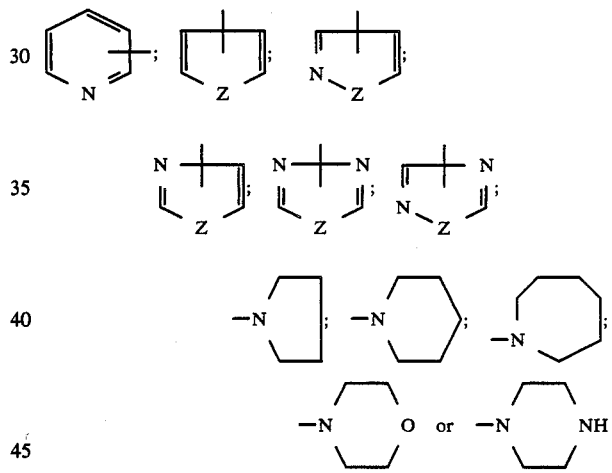

where Z in each case represents oxygen or sulphur and where suitable substituents are: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio; and in addition in each case straight-chain or branched alkoxy having 1 to 6 carbon atoms, alkenyloxy having 3 to 6 carbon atoms or alkinyloxy having 3 to 6 carbon atoms, or optionally straight-chain or branched benzyl, phenylethyl, phenylpropyl, phenylbutyl, phenylpentyl, phenylhexyl, phenylheptyl, phenylcyanomethyl, phenylcyanoethyl, phenylcyanopropyl, benzyloxy, phenylethoxy, phenoxy, benzoyl, phenyl or naphthyl, which are each optionally monosubstituted to trisubstituted by identical or different substituents, suitable substituents on phenyl being in each case: fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl and phenoxy or $R^3$ and $R^4$, together with the nitrogen atom to which they are bonded, represent a heterocycle of the formula

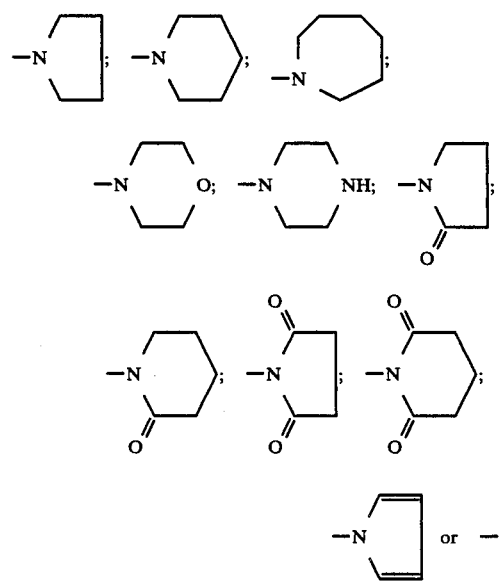

which is optionally monosubstituted to trisubstituted by identical or different substituents, suitable substituents being: methyl, ethyl, n- or i-propyl, chlorine or trifluoromethyl, X represents oxygen or sulphur and
Y represents oxygen or sulphur,
where X only represents sulphur, however, when at least one of the radicals $R^3$ or $R^4$ does not simultaneously represent hydrogen, methyl or ethyl.

The following substituted triazolinones of the general formula (I)

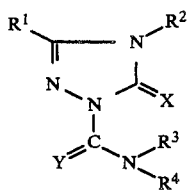

may be individually mentioned in addition to the compounds mentioned in the preparation examples:

TABLE 1

| $R^1$ | $R^2$ | $R_3$ | $R^4$ | X | Y |
|---|---|---|---|---|---|
| CH₃ | C₂H₅ | H | —CH(CH₃)₂ | O | O |
| CH₃ | C₂H₅ | H | —CH(CH₃)₂ | O | S |
| CH₃ | CH₃ | H | —C(CH₃)₃ | O | S |
| CH₃ | CH₃ | H | —C(CH₃)₃ | S | S |
| CH₃ | C₂H₅ | H | —CH(CH₃)₂ | S | O |
| CH₃ | CH₃ | H | —C(CH₃)(CH₂Cl)CH₃ | S | O |
| C₂H₅ | CH₃ | H | —C(CH₃)₃ | S | O |
| C₂H₅ | CH₃ | H | —C(CH₃)₃ | O | S |

TABLE 1-continued

| $R^1$ | $R^2$ | $R_3$ | $R^4$ | X | Y |
|---|---|---|---|---|---|
| C₂H₅ | CH₃ | H | —C(CH₃)(CH₂Cl)CH₃ | O | S |
| C₂H₅ | CH₃ | H | —C(CH₃)(CH₂Cl)CH₃ | S | O |
| C₂H₅ | CH₃ | H | —C(CH₃)(CN)C(CH₃)₃ | S | O |
| C₂H₅ | CH₃ | H | —CH(CN)C(CH₃)₃ | S | O |
| C₂H₅ | CH₃ | H | —C(CH₃)(CN)CH(CH₃)₂ | O | O |
| C₂H₅ | CH₃ | H | —C(CH₃)(CN)C₂H₅ | S | O |
| C₂H₅ | CH₃ | H | —C(CH₃)(CN)CH(CH₃)₂ | S | O |
| C₂H₅ | CH₃ | H | —C(CH₃)(CN)C₂H₅ | O | S |
| C₂H₅ | CH₃ | H | —C(CH₃)(CN)C₂H₅ | S | S |
| CH₃ | CH₃ | H | —*CH(CH₃)—C₆H₅(−) | O | S |
| CH₃ | CH₃ | H | —*CH(CH₃)—C₆H₅(−) | S | O |
| C₂H₅ | CH₃ | H | —*CH(CH₃)—C₆H₅(−) | O | S |
| C₂H₅ | CH₃ | H | —*CH(CH₃)—C₆H₅(−) | S | O |
| C₂H₅ | CH₃ | H | —CH(CN)-cyclopropyl | S | O |
| C₂H₅ | CH₃ | H | —CH(CN)-cyclopropyl | O | S |

TABLE 1-continued

| R¹ | R² | R₃ | R⁴ | X | Y |
|---|---|---|---|---|---|
| C₂H₅ | CH₃ | H | -CH(CN)-△ (cyclopropyl) | S | S |
| C₂H₅ | CH₃ | H | -CH(CN)-C₆H₁₁ | O | S |
| C₂H₅ | CH₃ | H | -CH(CN)-C₆H₁₁ | S | O |
| (CH₃)₂CH— | CH₃ | H | -C(CH₃)₃ | S | O |
| (CH₃)₂CH— | CH₃ | H | -C(CH₃)(C₂H₅)(CH₃) | S | O |
| (CH₃)₂CH— | CH₃ | H | -CH(CN)-C(CH₃)₃ | S | O |
| (CH₃)₂CH— | CH₃ | H | -CH(CN)-C(CH₃)₃ | O | S |
| (CH₃)₂CH— | CH₃ | H | -C(CH₃)(CN)-CH(CH₃)₂ | S | O |
| (CH₃)₂CH— | CH₃ | H | -C(CH₃)(CN)-CH(CH₃)₂ | O | S |
| (CH₃)₂CH— | CH₃ | H | -C(CH₃)(CH₂Cl)-CH₃ | O | S |
| (CH₃)₂CH— | CH₃ | H | -C(CH₃)(CH₂Cl)-CH₃ | S | O |
| (CH₃)₂CH— | CH₃ | H | -C(CH₂Cl)(CH₃)-CH₂Cl | S | O |
| (CH₃)₂CH— | CH₃ | H | -C(CH₂Cl)(CH₃)-CH₂Cl | O | S |
| CH₃ | CH₃ | H | -C(CH₂F)(CH₃)-CH₂F | S | O |
| CH₃ | CH₃ | H | -C(CH₃)(CF₃)-CH₃ | S | O |
| C₂H₅ | CH₃ | H | -C(CH₂F)(CH₃)-CH₂F | S | O |
| C₂H₅ | CH₃ | H | -C(CH₃)(CF₃)-CH₃ | S | O |
| C₂H₅ | CH₃ | H | -C(CH₂F)(CH₃)-CH₂F | O | S |
| C₂H₅ | C₂H₅ | H | -C(CH₃)₃ | O | O |
| C₂H₅ | C₂H₅ | H | -C(CH₃)(CN)-CH(CH₃)₂ | O | O |
| C₂H₅ | C₂H₅ | H | -C(CH₃)₃ | S | O |
| C₂H₅ | C₂H₅ | H | -C(CH₃)₃ | O | S |

If, for example, 1-chlorocarbonyl-3-ethoxymethyl-4-methyl-1,2,4-triazolin-5-one and allylamine are used as starting materials, then the course of the reaction of the process (a) according to the invention can be represented by the following equation:

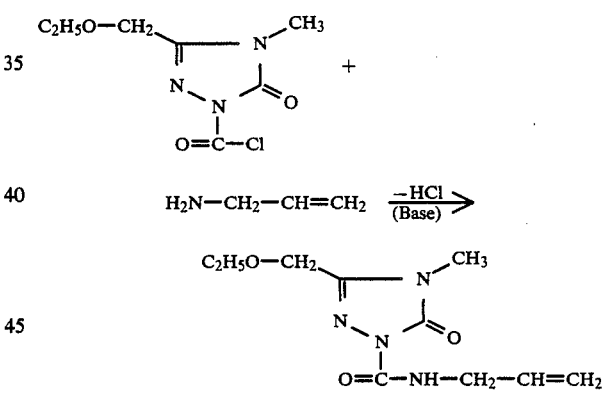

If, for example, 3,4-dimethyl-1-H-1,2,4-triazolin-5-one and isopropyl isocyanate are used as starting materials, then the course of the reaction of the process (b) according to the invention can be represented by the following equation:

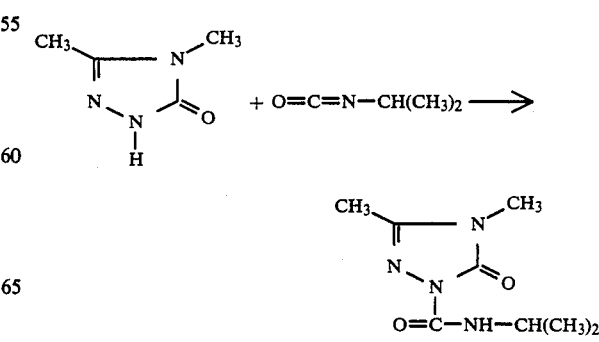

Formula (II) provides a general definition of the chloro(thio)carbonyltriazolinones required as starting materials for carrying out the process (a) according to the invention. In this formula (II), R¹, R², X and Y preferably or particularly preferably represent those radicals which have already been mentioned as preferred or particularly preferred for these substituents in connection with the description of the substances of the formula (I) according to the invention.

The chloro(thio)carbonyltriazolinones of the formula (II) are hitherto unknown.

They are obtained when 1-unsubstituted triazolinones of the formula (IV)

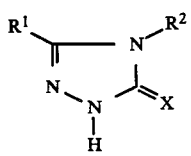   (IV)

in which
R1, R² and X have the above-mentioned meaning, are reacted with (thio)phosgene of the formula (VI)

   (VI)

in which
Y has the above-mentioned meaning, if desired in the presence of a diluent such as, for example, toluene or acetonitrile and if desired in the presence of an acid-binding agent such as, for example, triethylamine, at temperatures between +20 C. and +150 C.

Formula (III) provides a general definition of the amines furthermore required as starting materials for carrying out the process (a) according to the invention. In this formula (III), R³ and R⁴ preferably represent those radicals which have already been mentioned as preferred for these substituents in connection with the description of the substances of the formula (I) according to the invention.

The amines of the formula (III) are generally known compounds of organic chemistry.

Formula (IV) provides a general definition of the 1-unsubstituted triazolinones required as starting materials for carrying out the process (b) according to the invention and for the synthesis of the precursors of the formula (II). In this formula (IV), R¹, R² and X preferably represent those radicals which have already been mentioned as preferred for these substituents in connection with the description of the substances of the formula (I) according to the invention.

The 1-unsubstituted triazolinones of the formula (IV) are partly known (compare, for example, Chem. Ber. 98, 3034 [1965]; Bull. Soc. Chim, Fr. 1975, 1191; Bull. Soc. Chim. Fr. 1962, 1365; DE-OS (German Published Specification) No. 2,336,827).

The known, as well as the unknown compounds of the formula (IV) are obtained analogously to known processes (compare for example, Arch. Pharm. 301, 827 [1968]; J. Heterocycl. Chem. 15, 237 [1978]; Tetrahedron 32, 2347 [1976]; Roczn. Chem. 42, 247 [1968]and also the preparation examples).

Formula (V) provides a general definition of the iso(thio)cyanates furthermore required as starting materials for carrying out the process (b) according to the invention. In this formula (V), R⁴ and Y preferably represent those radicals which have already been mentioned as preferred for these substituents in connection with the description of the substances of the formula (I) according to the invention.

The iso(thio)cyanates are generally known compounds of organic chemistry (compare, for example, Saul Patai, "The Chemistry of Cyanates and their Thioderivatives" J. Wiley & Sons, New York 1977).

Preferred suitable diluents for carrying out the process (a) according to the invention are inert organic solvents. In particular these include aliphatic, alicyclic or aromatic, optionally halogenated hydrocarbons, such as, for example, benzine, ligroin, benzene, toluene, xylene, chlorobenzene, petroleum ether, pentane, hexane, heptane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones such as acetone or butanone, nitriles, such as acetonitrile or propionitrile, amides, such as dimethylformamide, dimethylacetamide, Nmethylformanilide, N-methylpyrrolidone or hexamethylphosphoric triamide, esters, such as ethyl acetate or bases such as pyridine.

If desired, the process (a) according to the invention is carried out in the presence of a suitable acid-binding agent. Those which are suitable are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU). It is also possible to employ the amine of the formula (III) used as the reactant in a suitable excess simultaneously as the acid-binding agent.

The reaction temperatures can be varied within a relatively wide range when carrying out the process (a) according to the invention. In general, the reaction is carried out at temperatures between 0° C. and +150° C., preferably at temperatures between +10° C. and +80° C.

The process (a) according to the invention is customarily carried out under atmospheric pressure. However, it is also possible to work at elevated pressure.

For carrying out the process (a) according to the invention, 1.0 to 5.0 mols preferably 1.0 to 2.5 mols, of amine of the formula (III) and if desired 1.0 to 2.5 mol of acid-binding agent are generally employed per mole of 1-chloro-(thio)carbonyl-triazolinone of the formula (II). The reaction is carried out and worked up and the reaction products are isolated analogously to generally known processes.

Suitable diluents for carrying out the process (b) according to the invention are likewise inert organic solvents. The diluents mentioned in process (a) are preferably used.

If desired, the process (b) according to the invention can be carried out in the presence of a basic reaction auxiliary. Those which are suitable are all customary inorganic and organic bases. Tertiary amines, such as triethylamine, N,N-dimethylaniline, pyridine, N,N-dimethylaminopyridine, diazabicyclooctane (DABCO), diazabicyclononene (DBN) or diazabicycloundecene (DBU) are preferably used. However, the addition of such catalysts is not compulsory.

The reaction temperatures can be varied within a relatively wide range when carrying out the process (b) according to the invention. In general, the reaction is carried out at temperatures between 0° C. and +150° C., preferably at temperatures between +40° C. and +120° C.

The process (b) according to the invention is customarily carried out under atmospheric pressure. However, it is also possible to work at elevated pressure, in particular with gaseous starting compounds.

For carrying out the process (b) according to the invention, 1.0 to 5.0 mols, preferably 1.0 to 2.5 mols, of iso(thio)cyanate of the formula (V) and if appropriate 1.0 to 2.5 mols, of reaction auxiliary are generally employed per mol of 1-unsubstituted triazolinone of the formula (IV). The reaction is carried out and worked up, and the reaction products are isolated analogously to generally known processes.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

In this case, the active compounds according to the invention can be employed with particularly good effect for combating dicotyledon weeds, in particular in monocotyledon cultures, such as, for example, corn.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, in the presence or absence of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as finely divided silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lining-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as a mixture with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beets and 4-amino-6-(1,1-dimethylethyl)-3-methylthio-1,2,4-triazin-5(4H)-one for combating weeds in soy beans. Mixtures with 2,4-dichlorophenoxyacetic acid; 2,4-dichlorophenoxypropionic acid; (2-methyl-4-chlorophenoxy)-acetic acid; (4-chloro-2-methylphenoxy)-propionic acid; 2-[4-(2,4-dichlorophenoxy)phenoxy]-propionic acid, its methyl or its ethyl ester; 2-{4-[(6-chloro-2-benzoxazolyl)-oxy]-phenoxy}propionic acid, its methyl or its ethyl ester; (trimethylsilylmethyl) 2-[4-(3,5-dichloropyrid-2-yloxy)phenoxy]-propionate; 3-(ethoxycarbonylaminophenyl)-N-(3'-methylphenyl)-carbamate; N-(1-ethylpropyl)-3,4-dimethyl-2,6-dinitroaniline; methyl 5-(2,4-dichlorophenoxy)-2-nitrobenzoate; N,N-dimethyl-N'-(4-isopropylphenyl)-urea; methyl 6,6-dimethyl-2,4-dioxo-3-[1-(2-propenyloxyamino)-butylidene]-cyclohexanecarboxylic acid; 2-[1-(ethoximino)butyl]-3-hydroxy-5-[tetrahydro-(2H)-thiopyran-3-yl]-2-cyclohexen-1-one; 2-[1-(ethoxamino)-butylidene]-5-(2-ethylthiopropyl)-1,3-cyclohexadione; methyl 2-[4,5-dihydro-4-methyl-4-(1-methylethyl)-5-oxo-1H-imidazol-2-yl]-4(5)-methylbenzoate; 2-15-methyl-5-(1-methylethyl)-4-oxo-2-imidazolin-2-yl]-3-quinolinecarboxylic acid; 3,5-dibromo-4-hydroxy-benzonitrile; 3,5-diiodo-4-hydroxybenzonitrile; N-methyl-2-(1,3-benzothiazol-2-yloxy)-acetanilide; methyl-3-[[[[(4-methoxy-6-methyl-1,3,5-triazin-2-yl)-amino]-carbonyl]-amino]-sulphonyl]-thiophene-2-carboxylate; 2-chloro-4-ethylamino-6-isopropylamino-1,3,5-triazine; 2-chloro-4-ethylamino-6-(3-cyanopropylamino)-1,3,5triazine; 3-isopropyl-2,1,3-benzothiadiazin-4-one-2,2-dioxide; 0-(6-chloro-3-phenyl-pyridazin-4-yl)-S-octylthiocarbonate or 4-(2,4-dichlorophenoxy)-butyric acid are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied not only before but also after emergence of the plants.

They can also be incorporated into the soil before sowing.

The amount of active compound used can vary within a relatively wide range. It depends essentially on the nature of the desired effect. In general, the amounts used are between 0.01 and 10 kg of active compound per hectare of soil surface, preferably between 0.05 and 5 kg per ha.

USE EXAMPLES

Example 1

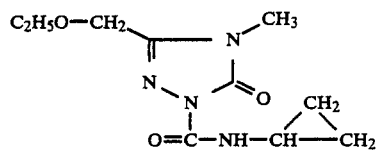

2.3 g (0.4 mol) of cyclopropylamine are added dropwise with stirring to 4.4 g (0.02 mol) of 1-chlorocarbonyl-3-ethoxymethyl-4-methyl-1,2,4-triazolin-5-one in 80 ml of dichloromethane so that the reaction temperature does not exceed 40° C. After completion of the addition, the mixture is stirred for four hours at room temperature, and the precipitated cyclopropylamine hydrochloride is then filtered off, and the filtrate is concentrated in vacuo, and the oily residue is taken up in 150 ml of dichloromethane, washed three times with 50 ml of water in each case, dried over sodium sulphate and the solvent is removed in vacuo.

4.2 g (88 % of theory) of 1-cyclopropylaminocarbonyl-3-ethoxymethyl-4-methyl-1,2,4-triazolin-5-one are obtained as an oil; $^1$H-NMR (CDCl$_3$/TMS) $\delta=2.85$ ppm (m; 1H).

PREPARATION OF THE STARTING COMPOUNDS

Example II-1

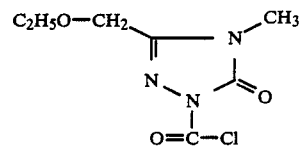

15.7 g (0.1 mol) of 3-ethoxymethyl-4-methyl-1H-1,2,4-triazolin-5-one in 150 ml of acetonitrile are warmed to 80° C. while introducing phosgene. In total, 20 g (0.2 mol) of phosgene are introduced. A brisk evolution of hydrogen chloride occurs from 60° C. After completion of phosgene introduction, the mixture is stirred for a further 5 hours at 80° C., and excess phosgene and hydrogen chloride are removed by purging with nitrogen and the mixture is filtered at 20° C. The filtrate is stirred with 1 l of cyclohexane, and the precipitated product is filtered off with suction, washed using cyclohexane and dried.

18.2 g (82 % of theory) of 1-chlorocarbonyl-3-ethoxymethyl-4-methyl-1,2,4-triazolin-5-one of melting point m.p. 107° C. are obtained.

Example IV-1

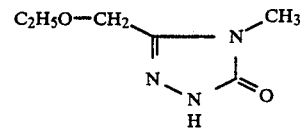

50 g (0.23 mol) of ethoxyacetic anhydride are added with stirring and ice-cooling to 23.4 g (0.26 mol) of 4-methylsemicarbazide in 500 ml of dichloromethane, and the mixture is stirred for 15 hours at room temperature after completion of the addition and then evaporated in vacuo. 15 g of sodium hydroxide are added to the crude product thus obtainable in 800 ml of water, and the mixture is stirred for 3 hours at 100° C., neutralized with dilute hydrochloric acid and concentrated in vacuo. The residue is taken up in 700 ml of ethyl acetate/ethanol (1:1), filtered, and the filtrate is again concentrated and the remaining oil is crystallized by trituration with ether.

24 g (59 % of theory) of 3-ethoxymethyl-4-methyl-1,2,4-(1H)-triazolin-5-one of melting point 92° C. are obtained.

EXAMPLE 2

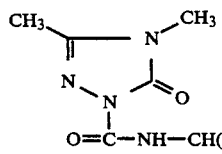

4.25 g (0.05 mol) of isopropyl isocyanate are added to 2.2 g (0.02 mol) of 3,4-dimethyl-1H-1,2,4-triazolin-5-one (compare Bull. Soc. Chim. Fr. 1975, 1191) in 100 ml of toluene and the mixture is stirred for 2 hours at 120° C. The cooled reaction mixture is filtered and the filtrate is concentrated in vacuo.

2.4 g (60 % of theory) of 1-isopropylaminocarbonyl-3,4-dimethyl-1,2,4-triazolin-5-one of melting point 81° C. are obtained.

The following substituted triazolinones of the general formula (I)

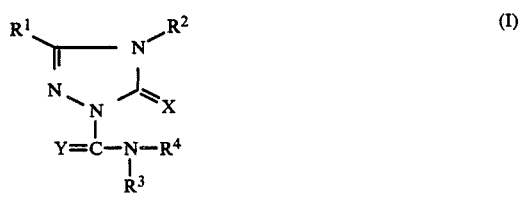

are obtained in a corresponding manner and according to the general instructions for preparation:

TABLE 2

| Example No. | $R^1$ | $R^2$ | $-N\begin{smallmatrix}R^3\\R^4\end{smallmatrix}$ | X | Y | Physical properties |
|---|---|---|---|---|---|---|
| 3 | CH₃ | CH₃ | —NH—CH(—C₆H₅)(CH₂)₃—CH₃ | O | O | ¹H-NMR*: 5.0 (m) |
| 4 | CH₃ | CH₃ | —NH—CH(CH₃)—C₂H₅ | O | O | ¹H-NMR*: 4.0 (m) |
| 5 | CH₃ | CH₃ | —NH—CH₂—CH(CH₃)₂ | O | O | m.p. 64° C. |
| 6 | CH₃ | CH₃ | —NH—(CH₂)₅—CH₃ | O | O | m.p. 41° C. |
| 7 | CH₃ | CH₃ | —NH—(CH₂)₃—OC₂H₅ | O | O | m.p. 70° C. |
| 8 | CH₃ | CH₃ | —NH—CH₂—C(CH₃)₃ | O | O | m.p. 63–66° C. |
| 9 | CH₃ | CH₃ | —NH—CH₂—C₆H₅ | O | O | m.p. 178° C. |
| 10 | C₂H₅ | CH₃ | —NH—CH(CH₃)₂ | O | O | m.p. 93° C. |
| 11 | CH₃ | CH₃ | —NH—*CH(CH₃)—C₆H₅ (+) | O | O | m.p. 110° C. |
| 12 | CH₃ | CH₃ | —NH—*CH(CH₃)—C₆H₅ (−) | O | O | m.p. 98° C. |
| 13 | C₂H₅ | CH₃ | —NH—*CH(CH₃)—C₆H₅ (+) | O | O | ¹H-NMR*: 5.2 (m) |

TABLE 2-continued $$-N\begin{matrix}R^3\\R^4\end{matrix}$$

| Example No. | $R^1$ | $R^2$ | $-N\begin{matrix}R^3\\R^4\end{matrix}$ | X | Y | Physical properties |
|---|---|---|---|---|---|---|
| 14 | $C_2H_5$ | $CH_3$ | $-NH-\overset{*}{CH}(CH_3)-C_6H_5$ (−) | O | O | $^1$H-NMR*: 5.2 (m) |
| 15 | $C_2H_5O-CH_2-$ | $CH_3$ | $-NH-CH(CH_3)_2$ | O | O | m.p. 80° C. |
| 16 | $C_2H_5O-CH_2-$ | $CH_3$ | $-NH-C(CH_3)_3$ | O | O | $^1$H-NMR*: 1.4 (s) |
| 17 | $CH_3$ | $CH_3$ | $-NH-C(CH_3)_3$ | O | O | m.p. 112–114° C. |
| 18 | $CH_3$ | $CH_3$ | $-NH-(CH_2)_2-OCH_3$ | O | O | $^1$H-NMR*: 3.4 (s) |
| 19 | $CH_3$ | $CH_3$ | $-NH-(CH_2)_2-CH_3$ | O | O | m.p. 58° C. |
| 20 | $CH_3$ | $CH_3$ | morpholino ($-N\underset{}{\bigcirc}O$) | O | O | $^1$H-NMR*: 3.6 (m) |
| 21 | $CH_3$ | $CH_3$ | $-NH-CH(CH_3)-C_6H_4-Cl$ | O | O | $^1$H-NMR*: |
| 22 | $CH_3$ | $CH_3$ | $-NH-CH(CH_3)-C_6H_4-Br$ | O | O | m.p. 84° C. |
| 23 | $CH_3$ | $CH_3$ | $-NH-CH(CH_3)-C_6H_4-F$ | O | O | m.p. 78° C. |
| 24 | $C_2H_5$ | $CH_3$ | $-NH-C_6H_{11}$ (cyclohexyl) | O | O | m.p. 103° C. |
| 25 | $C_2H_5$ | $CH_3$ | $-NH-CH(CH_3)-C_2H_5$ | O | O | m.p. 74° C. |
| 26 | $C_2H_5$ | $CH_3$ | $-NH-CH_2-CH(CH_3)_2$ | O | O | m.p. 67° C. |
| 27 | $C_2H_5$ | $CH_3$ | $-NH-C(CH_3)_3$ | O | O | m.p. 126° C. |
| 28 | $C_2H_5$ | $CH_3$ | $-NH-(CH_2)_5-CH_3$ | O | O | m.p. 37° C. |
| 29 | $C_2H_5$ | $CH_3$ | $-NH-(CH_2)_2-CH_3$ | O | O | m.p. 65° C. |
| 30 | $C_2H_5$ | $CH_3$ | $-NH-CH_2-C(CH_3)_3$ | O | O | m.p. 70° C. |
| 31 | $CH_3$ | $CH_3$ | $-NH-CH_2-C_6H_4-Cl$ | O | O | m.p. 96° C. |
| 32 | $C_2H_5$ | $CH_3$ | $-NH-C_5H_9$ (cyclopentyl) | O | O | m.p. 94° C. |
| 33 | $C_2H_5$ | $CH_3$ | $-NH-(CH_2)_2-CH(CH_3)_2$ | O | O | $^1$H-NMR*: 1.5 (m) |
| 34 | $C_2H_5$ | $CH_3$ | $-NH-CH_2-CH(CH_3)-C_2H_5$ | O | O | m.p. 49° C. |
| 35 | $C_2H_5$ | $CH_3$ | $-NH-(CH_2)_3-N(CH_3)_2$ | O | O | $^1$H-NMR*: 2.2 (s) |

TABLE 2-continued

| Example No. | R¹ | R² | -N(R³)(R⁴) | X | Y | Physical properties |
|---|---|---|---|---|---|---|
| 36 | $C_2H_5$ | $CH_3$ | $-NH-(CH_2)_4-CH_3$ | O | O | $^1$H-NMR*: 3.4 (q) |
| 37 | $C_2H_5$ | $CH_3$ | -NH-(2-methylcyclohexyl) 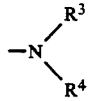 | O | O | m.p. 74° C. |
| 38 | $C_2H_5$ | $CH_3$ | -NH-(4-methylcyclohexyl) 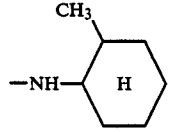 | O | O | m.p. 94° C. |
| 39 | $C_2H_5$ | $CH_3$ | $-NH-CH_2-CH_2-Cl$ | O | O | m.p. 98° C. |
| 40 | $C_2H_5$ | $CH_3$ | $-NH-(CH_2)_2-$(2-pyridyl) 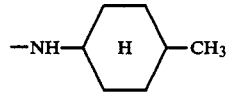 | O | O | m.p. 61° C. |
| 41 | $C_2H_5$ | $CH_3$ | -NH-(3-methylcyclohexyl) 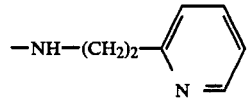 | O | O | m.p. 102° C. |
| 42 | $C_2H_5$ | $CH_3$ | $-NH-CH_2-CH_2-$morpholino 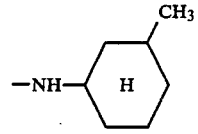 | O | O | $^1$H-NMR* 3.7 (m) |
| 43 | H | $CH_3$ | $-NH-CH(CH_3)_2$ | O | O | m.p. 167° C. |
| 44 | H | $CH_3$ | -NH-cyclohexyl 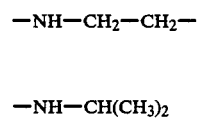 | O | O | m.p. 168° C. |
| 45 | H | $CH_3$ | $-NH-CH(CH_3)-C_2H_5$ | O | O | m.p. 118° C. |
| 46 | H | $CH_3$ | $-NH-CH_2-CH(CH_3)_2$ | O | O | m.p. 167° C. |
| 47 | H | $CH_3$ | $-NH-C(CH_3)_3$ | O | O | m.p. 147° C. |
| 48 | H | $CH_3$ | -NH-cyclopentyl 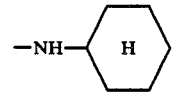 | O | O | m.p. 190° C. |
| 49 | H | $CH_3$ | $-NH-(CH_2)_2-CH(CH_3)_2$ | O | O | m.p. 161° C. |
| 50 | H | $CH_3$ | $-NH-CH_2-CH(CH_3)-C_2H_5$ | O | O | m.p. 134° C. |
| 51 | H | $CH_3$ | $-NH-CH^*(CH_3)-C_6H_5$ (+) 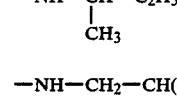 | O | O | m.p. 177° C. |

TABLE 2-continued

| Example No. | R¹ | R² | -N(R³)(R⁴) | X | Y | Physical properties |
|---|---|---|---|---|---|---|
| 52 | H | CH₃ | -NH-*CH(CH₃)-C₆H₅ (−) | O | O | m.p. 202° C. |
| 53 | (CH₃)₂CH— | CH₃ | -NH-CH(CH₃)₂ | O | O | m.p. 107° C. |
| 54 | C₂H₅O—CH₂— | CH₃ | -NH-cyclohexyl (H) | O | O | ¹H-NMR*: 3.8 (m) |
| 55 | C₂H₅O—CH₂— | CH₃ | -NH-(4-methylcyclohexyl) | O | O | ¹H-NMR*: 3.8 (m) |
| 56 | CH₃ | CH₃ | -NH-CH(CH₃)-CH=N-OCH₃ | O | O | ¹H-NMR* 4.7 (m) |
| 57 | C₂H₅ | CH₃ | -NH-CH(CH₃)-CH=N-OCH₃ | O | O | ¹H-NMR*: 4.7 (m) |
| 58 | H | CH₃ | -NH-CH(CH₃)-CH=N-OCH₃ | O | O | ¹H-NMR*: 4.7 (m) |
| 59 | C₂H₅O—CH₂— | CH₃ | -NH-*CH(CH₃)-C₆H₅ (−) | O | O | ¹H-NMR* 5.2 (m) |
| 60 | (CH₃)₂CH— | CH₃ | -NH-CH(CH₃)-C₂H₅ | O | O | m.p. 65° C. |
| 61 | (CH₃)₂CH— | CH₃ | -NH-C(CH₃)₃ | O | O | m.p. 131° C. |
| 62 | (CH₃)₂CH— | CH₃ | -NH-C(CH₃)₂-C₂H₅ | O | O | ¹H-NMR*: 0.9 (t) |
| 63 | (CH₃)₂CH— | CH₃ | -NH-cyclopentyl | O | O | m.p. 110° C. |
| 64 | (CH₃)₂CH— | CH₃ | -NH-cyclohexyl | O | O | m.p. 138° C. |
| 65 | (CH₃)₂CH— | CH₃ | -NH-cyclopropyl | O | O | m.p. 64° C. |
| 66 | (CH₃)₂CH— | CH₃ | -NH-*CH(CH₃)-C₆H₅ (+) | O | O | ¹H-NMR*: 5.2 (m) |

TABLE 2-continued

| Example No. | R¹ | R² | -N(R³)(R⁴) | X | Y | Physical properties |
|---|---|---|---|---|---|---|
| 67 | (CH₃)₂CH— | CH₃ | —NH—*CH(CH₃)—C₆H₅ (−) | O | O | ¹H-NMR*: 5.2 (m) |
| 68 | CH₃ | CH₃ | —NH-cyclopropyl | O | O | m.p. 147–150° C. |
| 69 | CH₃ | CH₃ | —NH-cyclohexyl (H) | O | O | m.p. 121–123° C. |
| 70 | CH₃ | CH₃ | —NH-cyclopentyl (H) | O | O | m.p. 91–92° C. |
| 71 | C₂H₅ | CH₃ | —NH—C(CH₃)(C₂H₅)(CH₃) | O | O | m.p. 87° C. |
| 72 | C₂H₅ | CH₃ | —NH—C(C₂H₅)(CH₃)(C₂H₅) | O | O | m.p. 90° C. |
| 73 | C₂H₅ | CH₃ | —NH—C(CH₃)(C(CH₃)₃)(CH₃) | O | O | m.p. 93° C. |
| 74 | C₂H₅ | CH₃ | —NH—C(CH₃)(C≡CH)(CH₃) | O | O | m.p. 154° C. |
| 75 | C₂H₅ | CH₃ | —NH—C₆H₅ | O | O | m.p. 170° C. |
| 76 | C₂H₅ | CH₃ | —NH—C(CN)(C(CH₃)₃)(CH₃) | O | O | |
| 77 | C₂H₅ | CH₃ | —NH—C(CH₂Cl)(CH₃)(CH₂Cl) | O | O | m.p. 97° C. |
| 78 | C₂H₅ | CH₃ | —NH—C(CH₃)(CH₂Cl)(CH₃) | O | O | m.p. 106° C. |
| 79 | C₂H₅ | CH₃ | —NH—C(CH₃)(CHCl₂)(CH₃) | O | O | |
| 80 | C₂H₅ | CH₃ | —NH-cyclopropyl | O | O | ¹H-NMR*: 2.8 (m) |

TABLE 2-continued $$-N\begin{subarray}{c}R^3\\ R^4\end{subarray}$$

| Example No. | $R^1$ | $R^2$ | $-N{<}^{R^3}_{R^4}$ | X | Y | Physical properties |
|---|---|---|---|---|---|---|
| 81 | $C_2H_5$ | $CH_3$ | 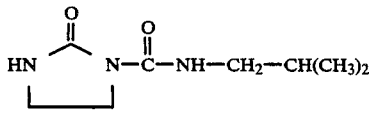 | O | O | $^1$H-NMR:* 3.8 (m) |
| 82 | $C_2H_5$ | $CH_3$ | $-NH-CH_2-C_6H_5$ | O | O | m.p. 143°–145° C. |
| 83 | $C_2H_5$ | $CH_3$ | $-NH-(CH_2)_3-OC_2H_5$ | O | ) | |

*The $^1$H-NMR spectra were recorded in deuterochloroform (CDCl$_3$) using tetramethylsilane (TMS) as internal standard. The chemical shift is given as the δ value in ppm.

USE EXAMPLES

The compound shown below was employed as the comparison substance in the following use example:

$$\text{(A)} \quad \underset{\underset{\displaystyle |_____|}{}}{HN\overset{O}{\overset{\|}{C}}\!-\!N\!-\!\overset{O}{\overset{\|}{C}}\!-\!NH\!-\!CH_2\!-\!CH(CH_3)_2}$$

N-isobutyl-imidazolidin-2-one-1-carboxamide (known from K. H. Büchel, "Pflanzenschutz und Schädlingsbekämpfung" ("Plant Protection and Pest Combating"), p. 170, Thieme Verlag Stuttgart 1977).

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

The clearly superior activity against weeds such as, for example, Abutilon, Datura and Galinsoga with comparable selectivity for useful plants compared to the comparison substance (A) is shown in this test, for example, by the compounds of the following preparation examples: (22) and (27).

It is understood that the specification and examples are illustrative but not limitative of the present invention and that other embodiments within the spirit and scope of the invention will suggest themselves to those skilled in the art.

We claim:
1. A substituted triazolinone of the formula

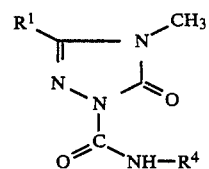

in which
$R^1$ is $C_{1-4}$-alkyl, and
$R^4$ is $C_1$-$C_8$-alkyl, $C_3$-$C_8$cycloalkyl, $C_2$-$C_8$alkynyl or is phenylalkyl with 1 to 7 carbon atoms in the straight-chain or branched alkyl part, which are each optionally substituted on the phenyl by identical or different substituents selected from the group consisting of fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl and phenoxy.

2. A compound according to claim 1, wherein such compound is 1-[1-(6-bromophenyl)-ethylaminocarbonyl]-3,4-dimethyl-1,2,4-triazolin-5-one of the formula

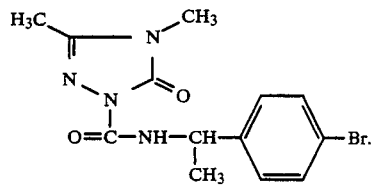

3. A compound according to claim 1 wherein such compound is 1-t-butylaminocarbonyl-3-ethyl-4-methyl-1,2,4-triazolin-5-one of the formula

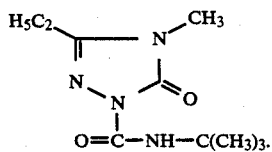
4. A herbicidal composition comprising a herbicidally effective amount of a compound according to claim 1 and an inert diluent.
5. A method of combating unwanted vegetation which comprises applying to such vegetation or to a locus from which it is desired to exclude such vegetation a herbicidally effective amount of a compound according to claim 1.
* * * * *